United States Patent [19]

Glassman

[11] 4,022,210
[45] May 10, 1977

[54] DISPOSABLE DIAPER WITH A SUPPLEMENTAL INSERT

[76] Inventor: Jacob A. Glassman, 1680 Meridian Ave., Miami Beach, Fla. 33139

[22] Filed: Aug. 11, 1975

[21] Appl. No.: 603,442

[52] U.S. Cl. .............................. 128/284; 128/287
[51] Int. Cl.² ...................................... A61F 13/16
[58] Field of Search ............ 128/284, 287, 290 H, 128/290 R, 290 P, 268

[56] References Cited

UNITED STATES PATENTS

| | | | |
|---|---|---|---|
| 2,002,368 | 5/1935 | Fancher | 128/284 |
| 2,450,789 | 1/1948 | Frieman | 128/284 |
| 2,481,351 | 9/1949 | Rosenfield | 128/290 H |
| 3,050,063 | 8/1962 | Margraf | 128/284 |
| 3,430,629 | 3/1969 | Murphy | 128/284 |
| 3,521,624 | 7/1970 | Gander et al. | 128/268 |
| 3,554,195 | 1/1971 | Murdoch | 128/284 |
| 3,572,342 | 3/1971 | Lindquist et al. | 128/287 |
| 3,595,235 | 7/1971 | Jespersen | 128/284 |
| 3,693,621 | 9/1972 | Jarusik | 128/287 |
| 3,794,034 | 2/1974 | Jones, Sr. | 128/290 R |

*Primary Examiner*—Aldrich F. Medbery
*Attorney, Agent, or Firm*—Elmer L. Zwickel

[57] ABSTRACT

A disposable diaper having a removable laminated supplemental insert formed with a pull tab to permit its separation from the diaper. Both the diaper and insert have means to insure spreading of any moisture deposited thereon. The insert also includes means to initially hold the margins of the diaper folded thereover.

11 Claims, 11 Drawing Figures

U.S. Patent  May 10, 1977  Sheet 1 of 2  4,022,210
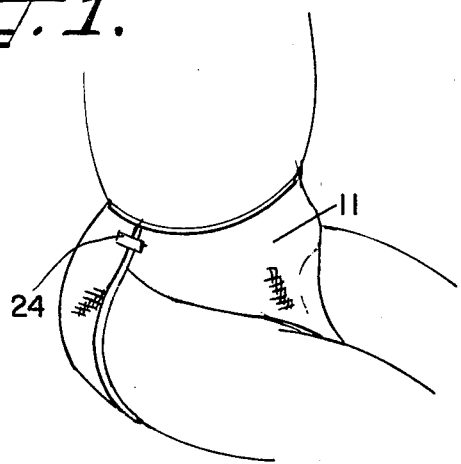
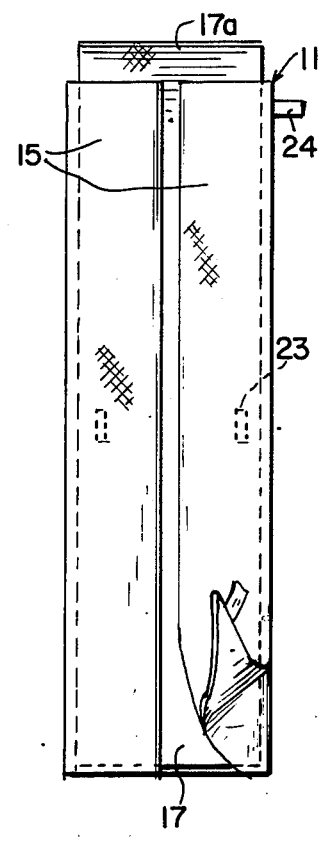
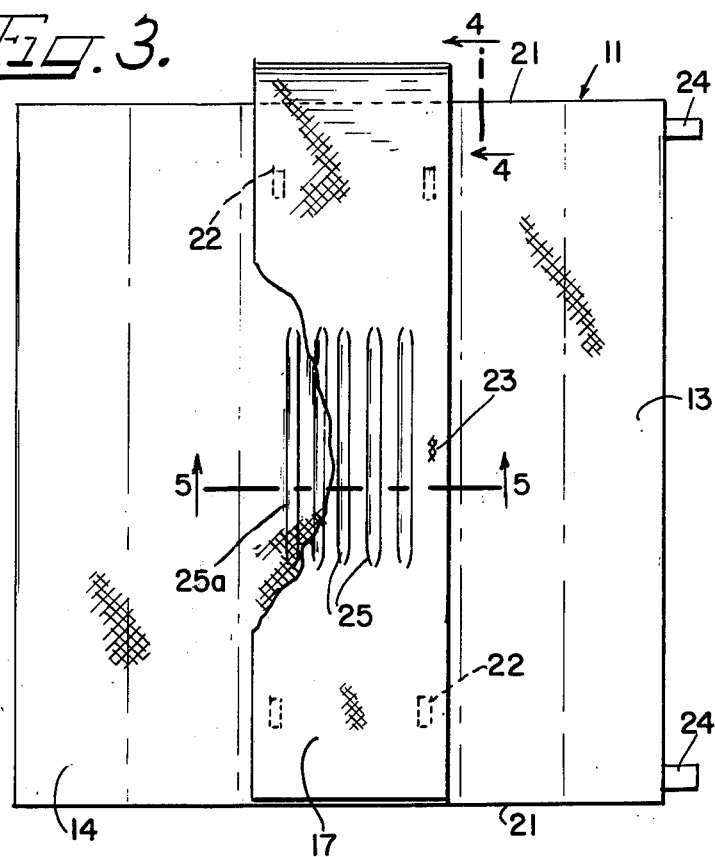
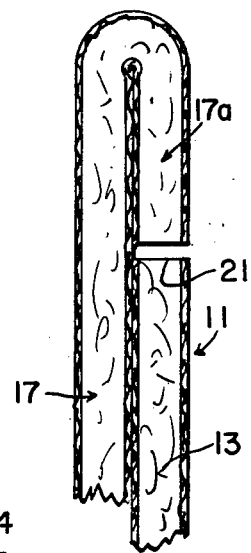
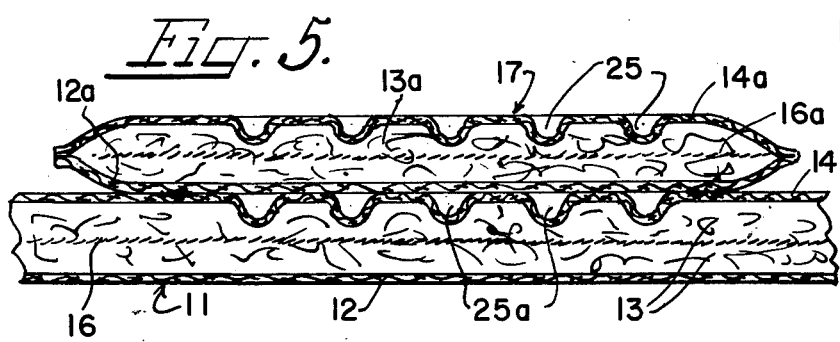

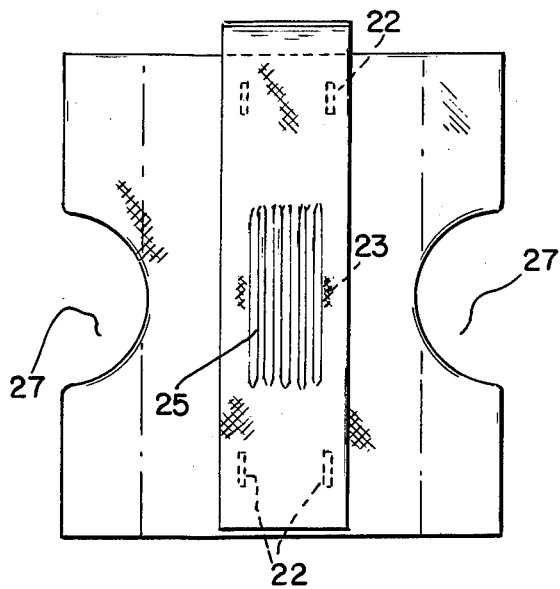
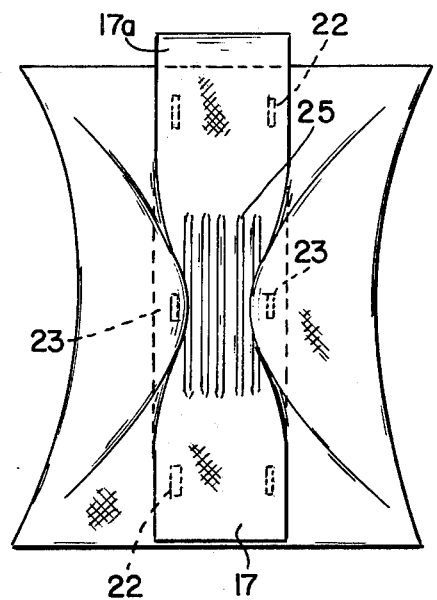
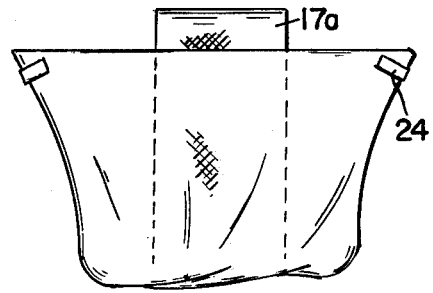
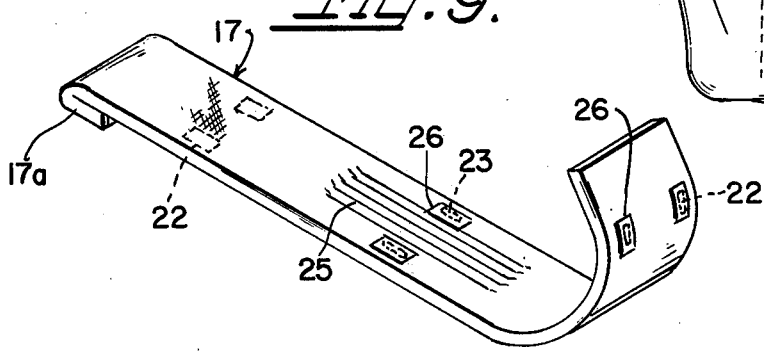
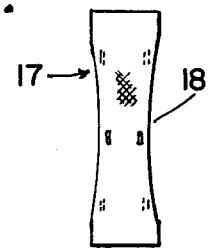
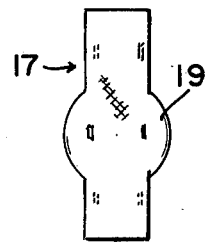

DISPOSABLE DIAPER WITH A SUPPLEMENTAL INSERT

The invention relates to improvements in disposable diapers and is characterized by having a supplemental laminated strip insert including a moisture absorbent material removably secured to the inside face of the disposable diaper and wherein the supplemental strip and the diaper are provided with means to insure wide distribution of moisture throughout their central areas. The strip is also characterized by having a thickened tab portion on or attached to one end so as to facilitate finger engagement therewith when the strip is to be withdrawn from the disposable diaper. Further, the strip is provided with adhesively coated areas on both its top and bottom faces, normally covered by a removable covering strip, which adhesive functions to retain the diaper in a folded condition prior to use and to maintain its associated strip detachably secured thereto.

The invention constitutes an improvement over the disposable diaper shown and claimed in my co-pending application Ser. No. 592,406, filed July 21, 1975.

Conventional disposable diapers now available on the market embody a laminated one-piece structure composed of a thin bottom or outer layer of moisture impervious material and a relatively thick inner layer or layers of moisture absorbent material, all of substantially uniform size. In use, when such diaper becomes wetted or soiled and therefore unsuited for further use, the entire diaper had to be replaced by a new clean dry diaper. This proceedure is costly, bothersome, annoying and irritating, not only to the wearer but also to the attendant changing the diaper. In the present instance the diaper is fitted with a readily removable supplemental laminated strip of longitudinally centrally placed material which is considerably less in width than the diaper but of a length that locates at least one end thereof in position outside the diaper to be readily grasped for pulling the strip out from the diaper.

The supplemental or insert strip extends from front to back of the diaper when it is being worn. This enables an attendant, upon observance that the strip has become wetted or soiled, to grasp the strip and gently pull it out and away from the diaper without diaper removal, hence the wearer is not disturbed and the attendant is saved the need to change diapers inasmuch as the diaper per se, after removal of the soiled top supplemental strip, is now relatively dry and fresh and hence has a new and prolonged servicable life.

Further, the removable laminated strip may be separately fabricated and merchandised for insertion by the purchaser into any disposable diaper now in general use. Such diapers are usually merchandised in a pre-folded condition with spot adhesive means securing the fold in place. To insert the removable supplemental strip, the adhesive joining of the fold is ruptured, the diaper is unfolded and the removable supplemental strip placed upon the diaper. The diaper is then re-folded over the strip and secured folded by the presence of a non-toxic pressure sensitive adhesive on select areas of the supplemental strip; thereby imparting the original fixed form of the pre-folded diaper.

It is therefore an object of the invention to provide a disposable diaper embodying one or more of the features hereinbefore referred to.

Another object is to provide a removable disposable supplemental diaper insert with means to detachably retain it in place upon a diaper and/or to hold the diaper in its prefolded condition prior to use.

Another object is to provide means in a diaper insert to insure widespread distribution of moisture deposited thereon.

Another object is to provide a removable supplemental diaper insert for a disposable diaper with an attached pull tab.

Other objects and advantages of the invention will become apparent with reference to the following specification and accompanying drawings.

IN THE DRAWINGS:

FIG. 1 is a representative perspective view of the improved diaper fitted upon an infant.

FIG. 2 is a plan view of one form of diaper embodying the invention and folded prior to use.

FIG. 3 is a plan view of the FIG. 2 diaper opened for use, and showing the supplemental insert partially broken away.

FIG. 4 is a detail view showing the pull tab, as viewed along line 4—4 of FIG. 3.

FIG. 5 is a fragmentary sectional view of the diaper and supplemental insert, taken substantially on line 5—5 of FIG. 3.

FIG. 6 is a view of a diaper like the one shown in FIG. 3, with its side edges recessed.

FIG. 7 is a plan view of another commercially made diaper, showing the supplemental insert in place thereon.

FIG. 8 is an elevational view of the FIG. 7 diaper, folded as when being worn.

FIG. 9 is a perspective view of the supplemental insert strip shown in FIG. 3.

FIGS. 10 and 11 are plan views of supplemental insert strips embodying different contours.

Referring now to the exemplary illustrations of the improved disposable diaper as shown in the accompanying drawings, and particulary in FIGS. 1 through 5, the diaper 11 is substantially rectangular in shape and is comprised of a thin bottom or outside layer 12 of moisture impervious material, and at least one thick layer 13 of highly moisture absorbent material, such as cotton, cellulose, scrim or other comparable material. These two layers, as well as an overlaying thin layer 14 of moisture absorption material are joined together around their peripheral edges. This diaper assembly, insofar as it has been described in this paragraph is quite common. Commercially, such a disposable diaper is provided in a compact form, that is, with its side portions or margins 15 folded (single or double) inwardly over the medial portion and the folded over side portions, generally indicated in FIG. 2, are temporarily secured by non-toxic spot adhesive.

However, applicant prefers to use two absorbent layers 13 (FIG. 5) with a quantity of deodorant and/or a medicament material 16 (powder) sandwiched between the layers 13. If one layer is elected, the deodorant and/or a medicament material 16 may be sandwiched between the top surface of the layer 13 and the overlying thin absorbent layer 14, or, in the alternative, in either instance the thin layer 14 may be impregnated with such material.

Applicant has further improved the commercial type of diaper by providing it with a removable supplemental insert strip 17 of the character best shown in FIG. 9. This strip 17, which is placed over the top surface of the longitudinal central portion of the diaper, is comprised of the same material as the diaper 11, it preferably being cut from the same laminated stock so as to have a moisture impervious thin bottom layer 12a, one or more thick layers 13a of moisture absorbent material and a thin covering layer 14a, with or without the medicament andor the deodorant material 16a. The supplemental insert strip may be of uniform width throughout its length as shown in FIGS. 3 and 9, or it may have its side edges at the medial portion recessed as at 18 (FIG. 10) or enlarged as at 19 (FIG.11).

The supplemental laminated insert strip 17 is substantially narrower than the diaper and is of a length slightly greater than the distance between the opposed straightaway extending end edges 21 of the diaper so as to protrude beyond one of said edges. The protruding end portion is folded over upon itself, as at 17a (FIG. 4) to provide a shoulder to assist positioning of the protruding end portion and to provide a strong pull tab to be engaged by the fingers for a purpose to be explained presently. The insert strip is provided at several points on its bottom face (side contacting the diaper) with a spot of non-toxic pressure sensitive adhesive 22 so as to be detachably secured to the diaper to hold it against displacement relative to the diaper. There are also at least two adhesive spots 23 on the top surface of the insert which serve to retain the diaper in the commercially pre-folded form shown in FIG. 2, prior to use. When the diaper is to be placed on the wearer, the folded over margins 15 are pulled out flat, the adhesive permitting this, as shown in FIG. 3, and when the diaper is in place as in FIG. 1, it may be secured by pins, snaps or by adhesive binding strips 24.

It will be noted that the supplemental strip 17 underlies the critical genital area of the wearer and, to insure widespread distribution of moisture (urine), the inside or body contacting surface of the strip 17 is formed with a series of channels 25 which may be formed by pressure application. This prevents puddling and avoids uncomfortable, premature saturation in the central critical area. As shown in FIG. 3, the diaper itself may be formed with such channels 25a.

Now, when the absorbent layer of the supplemental strip 17 becomes wetted or soiled, the attendant may grasp the pull tab 17a and by applying a slight tug can separate the supplemental strip from the diaper and withdraw same without removal of the diaper. As a consequence, the clean unsoiled or non-wetted diaper remains in place and in effect constitutes a fresh diaper. Thus, the improved diaper is in effect a double-duty diaper, and the infant is undisturbed by the withdrawal of the supplemental strip. Also, the annoyance and irritation of making frequent changes is minimized for the attendant.

In the FIG. 7-8 disclosure there is illustrated the application of the herein described supplemental strip 17 to another commercial form of diaper wherein the medial side portions of the diaper are brought inwardly toward each other in the central area thereof to overlie the strip 17 and be secured in place by the easily rupturable adhesive spots 23 on the strip.

In instances where it is desired to commercialize the supplemental strips apart from the diaper, for diaper insertion by the purchaser, the adhesive spots 22 and 23 are covered by sections 29 (FIG. 9) of a covering material which can be easily stripped off to expose the spot adhesive for use. Also, if desired, as shown in FIG. 6, the side edges of the diaper can be centrally recessed, as at 27, to aid in contour conformance with the thighs of a wearer.

Although I have described preferred embodiments of the invention, in considerable detail, it will be understood that the description thereof is intended to be illustrative, rather than restrictive, as details of the structure can be modified or changed without departing from the spirit or scope of the invention.

Accordingly, I do not desire to be restricted to the exact construction described and shown.

I claim:

1. A double-duty diaper comprising, in combination, a main diaper having a fluid-pervious cover sheet, a fluid impervious backing sheet and having located therebetween a pad including at least one relatively thick, substantially rectangular layer of highly moisture-absorbent material having a longitudinal central portion, a detachable insert strip of less width than the main diaper comprising a fluid pervious cover sheet, a fluid impervious backing sheet and having located therebetween a highly moisture absorbent material said insert strip being superimposed on said longitudinal central portion and being lightly adhered to the inner surface of said one layer, means on said main diaper for securing same about the waist of a human body with said insert strip in position thereon to contact the body, and means comprising a portion of said insert strip for removing said insert strip from the main diaper without corresponding removal or impairment of the diapering potential of said main diaper comprising said insert strip having a length relative to said main diaper such that at least one end of the insert strip extends beyond a related end edge of the main diaper, said extended end being folded upon itself to provide a reinforced pull tab.

2. A double-duty diaper according to claim 1, wherein the means for securing the main diaper about the waist portion is carried by the main diaper.

3. A double-duty diaper according to claim 1, wherein said related end edge of the main diaper extends straightway across said diaper, and said folded end of the insert strip extends beyond said straightway extending end edge.

4. The double-duty diaper according to claim 1, wherein said securing means comprises a readily rupturable adhesive means retaining the insert strip in position on the main diaper.

5. The double-duty diaper according to claim 1, wherein the folded extended end has a shoulder for abuttment with the related end edge of the diaper to insure placement of the insert strip.

6. The double-duty diaper according to claim 1, wherein the folded end portion defines a shoulder to abut the related end edge of the main diaper to maintain said end portion of the strip extended beyond said end edge.

7. The double-duty diaper according to claim 1, wherein the exposed baby contacting surface of the insert strip has moisture collecting recesses in the area midway its ends.

8. The double-duty diaper according to claim 7, wherein the recesses are longitudinal laterally spaced channels terminating short of the ends of the insert strip.

9. The double-duty diaper according to claim 1, wherein the side edges of said main diaper-forming layer of highly moisture absorbent material each has a recess provided in its mid-length portion as effects narrowing thereof throughout the extend of said mid-length portion, and said insert strip has width less than the width of the recessed mid-length portion of the main diaper.

10. The double-duty diaper according to claim 9, wherein the side portions of the main diaper extending beyond the insert strip are folded inwardly to overly the insert strip.

11. The double-duty diaper according to claim 10, wherein a rupturable adhesive holds the folded over side portions of the main diaper in position.

* * * * *